United States Patent
MacLauchlan (10) Patent No.: US 6,176,132 B1
(45) Date of Patent: Jan. 23, 2001

(54) METHOD FOR DETERMINING LIQUID LEVEL IN A CONTAINER USING AN ELECTROMAGNETIC ACOUSTIC TRANSDUCER (EMAT)

(75) Inventor: Daniel T. MacLauchlan, Lynchburg, VA (US)

(73) Assignee: BWX Technologies, Inc., Lynchburg, VA (US)

(*) Notice: Under 35 U.S.C. 154(b), the term of this patent shall be extended for 704 days.

(21) Appl. No.: 08/704,956

(22) Filed: Aug. 29, 1996

Related U.S. Application Data (62) Division of application No. 08/508,172, filed on Jul. 27, 1995, now Pat. No. 5,608,164.

(51) Int. Cl.[7] .................................................. G01F 23/28
(52) U.S. Cl. ........................................................ 73/290 V
(58) Field of Search ................................ 73/290 V, 597, 73/643, 52

(56) References Cited

U.S. PATENT DOCUMENTS

| | | | |
|---|---|---|---|
| 2,277,037 | 3/1942 | Clark et al. ............................ | 73/51 |
| 3,357,556 | 12/1967 | Martner et al. ....................... | 209/73 |
| 3,553,636 | 1/1971 | Baird .................................... | 340/1 |
| 3,802,252 | 4/1974 | Hayward et al. ..................... | 73/52 |
| 3,832,885 | 9/1974 | Hayward et al. ..................... | 73/52 |
| 3,913,383 | 10/1975 | Kreula et al. ......................... | 73/52 |
| 4,208,915 | 6/1980 | Edwards .............................. | 73/620 |
| 4,384,476 | 5/1983 | Black et al. .......................... | 73/61 |
| 4,535,627 | * 8/1985 | Prost et al. ........................... | 73/290 V |
| 4,580,448 | * 4/1986 | Skrgatic .............................. | 73/290 V |
| 4,821,573 | 4/1989 | Nagata et al. ....................... | 73/597 |
| 4,848,924 | 7/1989 | Nuspl et al. ......................... | 374/119 |
| 5,167,157 | 12/1992 | Wertz et al. ......................... | 73/627 |
| 5,372,042 | 12/1994 | Jarman et al. ....................... | 73/588 |

FOREIGN PATENT DOCUMENTS

| | | | |
|---|---|---|---|
| 58-92825 | * 6/1983 | (JP) ..................................... | 73/290 V |

OTHER PUBLICATIONS

Maxfield, B.W., A. Kuramoto & J.K. Hulbert, "Evaluating EMAT Designs for Selected Applications", *Materials Evaluation*, 45, Oct. 1987. Published by The American Society for Nondestructive Testing, Inc., 1987. pp. 1166–1183.

Thompson, R.B. & C.F. Vasile, "An elastic–wave ellipsometer for measurement of material property variations", *Appl. Phys. Lett.*, 34(2), Jan. 15, 1979. Published by American Institute of Physics, 1979. pp. 128–130.

* cited by examiner

*Primary Examiner*—John E. Chapman
(74) *Attorney, Agent, or Firm*—R. J. Edwards; Eric Marich; R. C. Baraona

(57) ABSTRACT

An ultrasonic method for determining liquid level in a container employs an electromagnetic acoustic transducer (EMAT) to launch and receive longitudinal ultrasonic waves into a thin metal wall or thin metal foil seal of the container, causing it to vibrate and launch ultrasonic compressional waves into liquid contained therein. The compressional waves travel through the liquid contents and reflect off an interface, returning to the thin metal wall and causing it to vibrate in the presence of the magnetic field produced by the EMAT transducer assembly. This induces a voltage in the eddy current coil of the EMAT transducer assembly, and by measuring a time of flight of the ultrasonic compressional waves through the liquid contents, and by using a preestablished value for a velocity of the ultrasonic compressional waves within the liquid contents, the liquid level of the contents can be determined.

1 Claim, 6 Drawing Sheets

METHOD FOR DETERMINING LIQUID LEVEL IN A CONTAINER USING AN ELECTROMAGNETIC ACOUSTIC TRANSDUCER (EMAT)

This is a division of application Ser. No. 08/508,172 filed Jul. 27, 1995 now U.S. Pat. No. 5,608,164.

FIELD AND BACKGROUND OF THE INVENTION

The present invention relates in general to the use of ultrasonics to inspect liquids in containers and, in particular, to a method and apparatus for ultrasonically inspecting liquids in containers to determine the condition of the liquids wherein the ultrasonic waves are produced by electromagnetic acoustic transducers (EMATs).

The use of ultrasonics to inspect liquids inside containers using conventional ultrasonic testing methods is well established in the art. In such testing, a piezoelectric (or similar) transducer is coupled to the wall of the container using some form of coupling media such a liquid. The ultrasonic sound waves then propagate through the wall of the container and into the liquid inside the container. The sound wave may then reflect from a solid object in the liquid, or a liquid-air interface, or the opposite wall of the container, and be detected by the ultrasonic transducer. In other applications, a pitch-catch arrangement of two transducers on opposite sides of the container is used to launch and detect the ultrasound. A wide range of measurements and liquids using ultrasonics is possible. Some of the possible measurements include liquid height, detection and imaging of solid objects in liquids (for example medical ultrasonic imaging of internal organs), velocity measurements of liquid flow, and attenuation measurements to determine the condition of the liquid.

Nagata et al. (U.S. Pat. No. 4,821,573) discloses a method and apparatus for ultrasonically inspecting the food contents of a package. An ultrasonic transmitter-receiver system is disposed on at least one side of the package and the occurrence or degree of degradation of the contents is determined based upon the output data from the system. The invention is stated to be particularly useful to inspect foods, pharmaceutical agents, feedstuffs and so-on, and they may be of any desired consistency but only if it is freely-flowable, such as a homogenous solution, a dispersion, a paste, or the like. Before the package is subjected to the ultrasonic inspection, it is preferably shaken so as to disperse the headspace (plenum within the packaging material) into the contents. However, depending upon the types of contents, the shaking process may be omitted. This system may be disposed either in contact with the exterior surface of the package or a short distance therefrom and may be disposed on the exterior wall surface of a water tank when the packages are subjected to ultrasonic inspection while immersed in water. Transmitters can be disposed on only one side of the package with the ultrasonic receiver on the other side, or the ultrasonic transmitter and receiver can both be disposed on the same side of the package so that the receiver receives a reflected ultrasonic wave. By measuring differences in sonic velocities between a transmission wave and a reception wave or the sonic velocity of a reception wave, the time from transmission to reception, and/or the degree of attenuation of the ultrasonic energy, the occurrence and degree of degradation of the contents can be evaluated. The useful wavelength of the ultrasonic waves disclosed is about 0.5 MHz to about 20 MHz. While only a single frequency can be employed at a given time, the accuracy of the evaluation is said to be improved by using a few selected frequencies for the transmission wave. Various sets of tests results based on measurements of reflected waves, transmitted waves, and the like are provided to show how various signals can be related to the condition of the food product contents.

As indicated in the various references cited on the face of Nagata et al., sonic or ultrasonic assessment of the condition of foodstuffs has been around for some time.

Clark et al. (U.S. Pat. No. 2,277,037) discloses a fruit ripeness tester which measures the degree of ripeness of fruit such as melons and pineapples by the measurement and calibration of the vibration characteristics of such objects.

Martner et al. (U.S. Pat. No. 3,357,556) discloses a method and apparatus for testing canned liquid material without removing the material from the can, and is particularly suited for the inspection of batch-prepared infant formula. The system is used to detect alterations in viscosity distribution such as by formation of curds or semi-solid bodies or the like, or increases in viscosity as a liquid material ages which is referred to as "age-thickening". The cans containing the liquid are rolled along a horizontal path at a preselected constant speed and in the path is disposed a narrow barrier having a height that is small with respect to the diameter of the can. By proper adjustment of the height of the barrier, cans containing a liquid material that is satisfactory will pass over the barrier whereas cans containing spoiled or aged-thickened contents will be arrested by the barrier. The "slushing" or flow pattern of the canned liquid material within the cans is responsible for cans "bouncing" off of the barrier and rolling backwardly.

Baird (U.S. Pat. No. 3,553,636) discloses a non-contacting ultrasonic interface viscosity and percent solid detecting device wherein the transducer is mounted out of contact with the processed liquid. Changes in ultrasonic attenuation characteristics are used as indications of changes in viscosity, percent solids, and/or interface level condition of the liquid contained within a vessel.

Kreula et al. (U.S. Pat. No. 3,913,383) discloses a method and apparatus for testing the contents of packages containing liquid product. Packages of interest are sealed is and contained liquid food products have physical properties that can change as a consequence of deterioration of the product. The package to be tested is placed on a movable support which is subjected to a sudden movement of short duration. A characteristic dependent on the movement of the support is detected, and signals are generated in response to the detected characteristics and compared with the preselected reference signals. In essence, the hydrodynamic behavior of the contents of the package are used to determine whether or not the contents have changed or spoiled.

Edwards (U.S. Pat. No. 4,208,915) discloses a method for determining foreign material in food products using ultrasonic sound. A plurality of transducers are disposed in a rotatable cylinder having a liquid couplant. The cylinder has a surrounding flexible wall which is compressed on top of the surface of the food products. The sound frequencies are transmitted through the food products and received back by a receiver in the transducers for monitoring any variance in the frequency which indicates foreign material in the food products. Black et al. (U.S. Pat. No. 4,384,476) discloses a method and apparatus for ultrasonically inspecting foodstuffs in which the fluid is passed through a curtain of ultrasonic sound. Reflection or absorption of the ultrasonic sound by extraneous materials is detected by ultrasonic sound receiving means and appropriate indication of such detection is given. The foodstuffs being inspected, however, are inspected as they flow pass the inspection point, and have not yet been packaged.

Jarman et al. (U.S. Pat. No. 5,372,042) discloses an ultrasonic inspection method for determining the seal integrity of the bond lines in sealed containers. These particular packages have a lid bonded to a container rim and it is the seal between the lid and the container that is to be inspected. The container rim is disposed between an ultrasonic transmitter system and an ultrasonic receiver system for inspection.

Wertz et al. (U.S. Pat. No. 5,167,157) discloses an ultrasonic method and apparatus for inspecting laminated products, particularly to determine the thickness of the innermost layers of the article. The mean of the measurements from each transducer placed on either side of the multilayered article is calculated to determine these thicknesses. The articles themselves are laminated plastic articles.

Hayward et al. (U.S. Pat. Nos. 3,832,885 and 3,802,252). Hayward et al. '885 discloses a method and apparatus for inspecting sealed containers, such as vacuum-packed cans of food, which involves repeatedly energizing electromagnetic transducer coils mounted in close proximity to the containers to cause the enclosures of the containers to vibrate at a frequency that is the function of the internal pressures within the container. Sounds produced by the vibrating enclosures provides a tonal pattern distinctive of the presence or absence of a container with an unsatisfactory internal pressure. Changes in the internal pressure are indicative of leakage or food spoilage or corrosion of the container. Hayward et al. '252 is drawn to an apparatus and method for monitoring the pressure or vacuum in a sealed container which consists of striking the can with a magnetic pulse of force to cause it to vibrate freely and thereby generate an acoustic ping sensed by an electrical pick-up device. The frequency of the ping is a function of the internal pressure in the container and the frequency spectrum of the signal output of the pick-up device is examined at a discriminator circuit to determine if the signal output contains selected frequencies at an energy level indicative of the desired pressure level. If not, the container is rejected. Measures are taken to render the signal output of the pick-up device insensitive to both the ambient noise and the large noise pulse generated while the can is being subjected to the magnetic pulse of force and also so that only the purest part of the signal generated in response to the acoustic ping is examined by the discriminator circuit.

A liquid or gel couplant is required for conventional ultrasonic testing of liquids in containers, which represents an additional cost. However, conventional ultrasonics using liquid or gel couplants are not practical at high temperatures. Additionally, in some cases, the surface of a container to be inspected may be contaminated with hazardous materials which would cause the couplant used in conventional ultrasonic testing to become contaminated requiring it to be treated as hazardous material for clean up and disposal. Finally, some metal or partially metal containers have an outer layer of non-conductive material such as paint, wrappers, labels, lids, or coating that would prevent the coupling of ultrasound into the container from a conventional ultrasonic transducer.

Electromagnetic acoustic transducers (EMATs) are sensors which are capable of launching and receiving sound waves in metals without a coupling media or even without contact with the surface of a workpiece being inspected. The ultrasound is launched and received in the surface of the metal by the interaction of magnet fields and eddy currents generated by the EMAT. EMATs are finding a wide range of nondestructive testing applications for metals. One previous application of EMATs to liquid measurements is known. In this case an EMAT was used to launch two types of plate wave modes in the metallic wall of a vessel containing a liquid. One mode was the N=1 Shear Horizontal (SH1) mode. The other mode was the N=0 Symmetric (SO) Lamb wave mode. The SH1 mode propagates in the wall of the vessel, producing only shearing displacements at the liquid-metal interface inside the vessel. Because a liquid cannot support a shear force, the SH1 mode is not attenuated by the liquid as it propagates. The SO mode produces substantial displacements normal to the surface of the metal at the metal-liquid interface as it propagates. Because a liquid does support compressional waves which are generated by displacements normal to the surface of the metal at the metal-liquid interface, the SO mode is attenuated by the liquid as it propagates. By placing a transmitter EMAT and a receiver EMAT a fixed distance apart vertically on the wall of the vessel, and measuring the relative amplitudes of the two modes, an indication of the liquid level between the two transducers can be obtained.

As previously noted, certain types of liquid containers have an outer layer that prevents inspection of the liquid contents therein using traditional ultrasonic techniques. Some containers are provided with outer plastic lids, caps or the like which leave an air gap between the outside surface of the container and the lid sealing the liquid contents. Traditional ultrasonic inspection techniques requiring physical coupling between the transducer and the workpiece being inspected cannot inspect through such air gaps. Some types of containers have thin metal walls or at least one thin metal foil wall.

It is thus apparent that an improved technique for the ultrasonic inspection of liquids in these types of containers is needed and would be welcomed by the industry.

SUMMARY OF THE INVENTION

The present invention overcomes the problems identified above, and other problems, and provides a method and apparatus which can be used to ultrasonically inspect liquids in containers having thin metal walls or at least one thin metal foil wall. The invention uses an electromagnetic acoustic transducer (EMAT) to generate the ultrasonic pulses. The couplants or gels used in conventional ultrasonic techniques are not required. This facilitates automated inspection of liquids in such containers, and eliminates measurement errors caused by the use of couplant and the necessity to clean the couplant from a container wall after testing. Naturally, the cost of providing the couplant for testing is also eliminated. Liquids in certain metal or partially metal containers at very high temperatures can be inspected because of the non-contact nature of the transducer.

A specially designed EMAT transducer assembly is disclosed and used to launch and receive longitudinal ultrasonic waves into a thin metal wall or a thin metal foil wall of a container, causing it to vibrate and launch ultrasonic compressional waves into the liquid contained therein. In contrast to applications of an EMAT to thick-walled inspections, the present invention is directed to the ultrasonic inspection/generation of longitudinal ultrasonic sound waves in very thin walled metal containers or metal parts of containers, and is particularly capable of generating longitudinal ultrasonic waves in a metal foil seal wall adhered to the other walls of a nonconductive vessel containing a liquid. As used herein, the distinction between thick-walled and thin-walled is that a thin-wall has a thickness that is much shorter than the ultrasonic wavelength that would be propagated through the metal forming the wall.

In each application, the generation mechanism for creating the ultrasonic waves is essentially the same. An EMAT is used to produce and to establish a magnetic field in the surface of the thin metal wall parallel to the surface. Radio frequency (RF) eddy currents are also induced by the EMAT in the surface of the thin metal wall. A Lorentz force is generated in the metal surface according to the vector product of J, the current density, and H, the magnetic field. If H and J both lie in the surface of the metal wall, the force generated by the interaction of the perpendicular components of the magnetic field H and the eddy currents J is directed normally to the surface of the metal wall. This normal force oscillates with the frequency of the induced eddy currents creating ultrasonic compressional waves which propagate normal to the surface of the thin metal wall.

In thin-walled containers or foils, where the thickness of the metal is much shorter than the ultrasonic wavelength in the metal, the generation and reception process is analogous to the operation of a loudspeaker in air. In this case, the thin metal wall or foil acts as a membrane, with the Lorentz forces generated in the wall or foil causing the metal membrane to vibrate, generating ultrasonic waves in the liquid. Because the thin wall or foil is much more compliant than a thick piece of metal, much larger displacements are generated at the metal-liquid interface than for a thick-wall case, resulting in much larger signal amplitudes. If a metal foil is adhered to a side of a non-conductive vessel, such as a plastic container, the EMAT can be used to launch and receive sound waves that propagate through the metal foil wall of the container, through the liquid, and return to the EMAT after reflection at a liquid-air or liquid-solid (wall) interface.

Accordingly, one aspect of the present invention is drawn to a method of ultrasonically inspecting liquid contents in a container to determine their condition, where the container has a thin metal wall forming at least one wall of the container. An electromagnetic acoustic transducer (EMAT) assembly is provided proximate to the thin metal wall to produce and cause a magnetic field to exist therein. An eddy current coil of the EMAT assembly is energized with an RF toneburst signal of known amplitude and frequency to generate a Lorentz force in the thin metal wall and cause it to vibrate and launch ultrasonic compressional waves into the liquid contents. The ultrasonic compressional waves are allowed to travel through the liquid contents and reflect off an interface. The reflected ultrasonic compressional waves return to the thin metal wall and cause it to vibrate in the presence of the magnetic field produced by the EMAT transducer assembly. The vibrations of the thin metal wall induce a voltage in the eddy current coil of the EMAT transducer assembly. An amplitude of the induced voltage in the eddy current coil is measured to determine the degree to which the ultrasonic compressional waves were attenuated during their passage through the liquid contents, the degree of attenuation being an indication of the condition of the liquid contents. The measured attenuation is then compared against preestablished values of attenuation representative of known conditions of the liquid contents to determine the condition of the liquid contents.

Another aspect of the present invention is drawn to a method of ultrasonically inspecting liquid contents in a container to determine a liquid level H therein, the container again having a thin metal wall forming at least one wall of the container. This method employs an EMAT assembly above, which is used to launch ultrasonic compressional waves into the liquid contents. The compressional waves travel through the liquid contents and reflect off an interface. The reflected ultrasonic compressional waves return to the thin metal wall and cause it to vibrate in the presence of the magnetic field produced by the EMAT transducer assembly. The vibrations of the thin metal wall induce a voltage in the eddy current coil of the EMAT transducer assembly. The time of flight of the ultrasonic compressional waves through the liquid contents is measured, and using a preestablished value for a velocity of the ultrasonic compressional waves within the liquid contents, the liquid level H of the liquid contents is calculated using the measured time of flight and the preestablished velocity value.

Other aspects of the present invention are drawn to various configurations of an electromagnetic acoustic (EMAT) transducer assembly for ultrasonically inspecting liquid contents in a container to determine their condition, the container having a thin metal wall forming at least one wall of the container. In a first embodiment, the EMAT transducer assembly comprises magnet means for producing a strong magnetic field across an air gap between portions of the magnet means, the magnet means causing a magnetic field to exist in the thin metal wall when the EMAT assembly is located proximate thereto. Mild steel yoke means provide a low reluctance magnetic field return path for the magnetic field. Flexible eddy current coil means, placed above and spaced from the magnet means by spacer means, receive an RF toneburst signal of known amplitude and frequency to generate a Lorentz force in the thin metal wall causing it to vibrate and launch ultrasonic compressional waves into the liquid contents. The flexible eddy current coil means has an arrangement of conductors such that electrical currents flowing through central conductors all flow in the same direction, while electrical currents in outer conductors flow in an opposite direction with respect to those in the central conductors, to create ultrasonic compressional waves with uniform polarity.

Other embodiments of the EMAT transducer assembly for use in the method of the present invention are also disclosed.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which preferred embodiments of the invention are illustrated and described.

DESCRIPTION OF THE PREFERRED EMBODIMENTS

Figure 1:
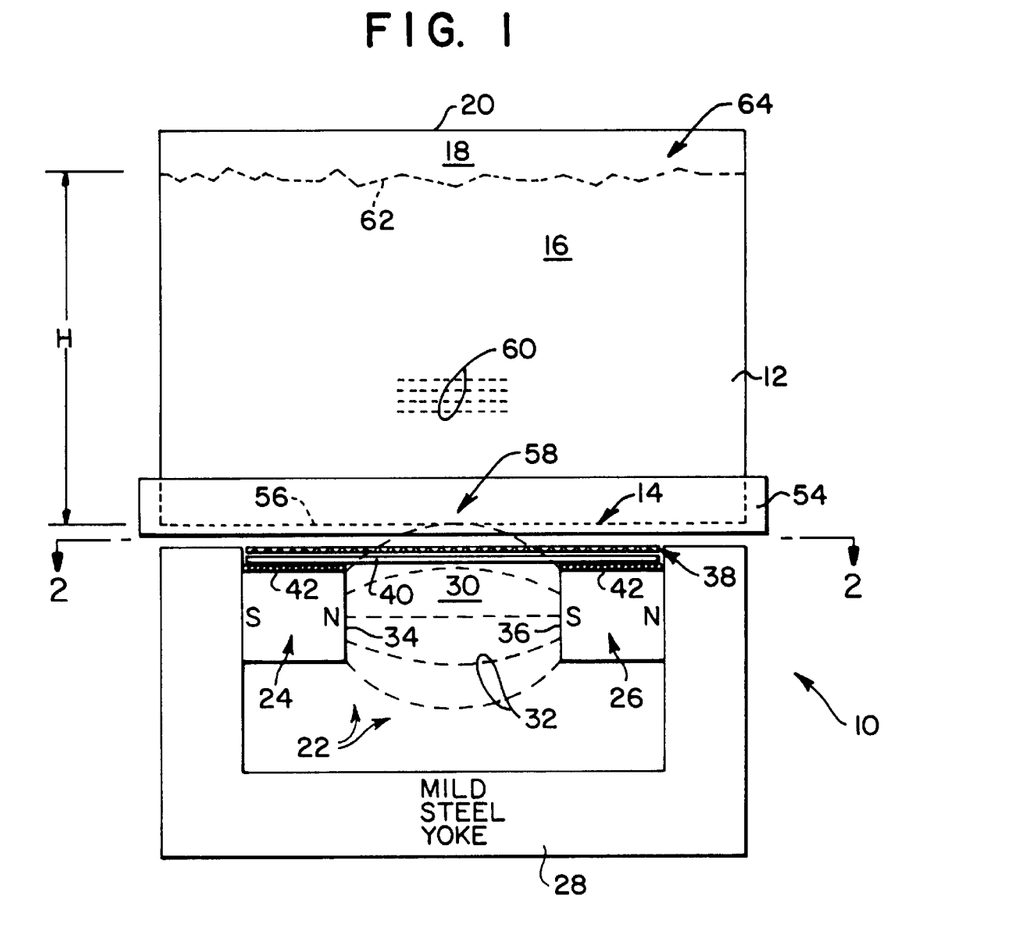
FIG. 1 is a schematic representation of an EMAT transducer assembly according to the present invention positioned to inspect the liquid contents of a plastic container with a metal foil seal.

Referring to the drawings generally, wherein like numerals designate the same or functionally similar elements throughout the several drawings, and to FIG. 1 in particular, there is shown a first embodiment of an EMAT transducer assembly 10 that has been reduced to practice for generating and receiving ultrasonic wave signals a plastic container or cup 12 having a metal foil seal 14 and containing a liquid 16. It is understood that while the present discussion is in the context of a plastic container or cup 12 having a thin metal foil seal 14, the present invention is equally applicable to the ultrasonic inspection of thin metal wall containers such as pop or beverage cans, soup cans, and the like. These containers may or may not have an outer layer of non-conductive material such as paint, wrappers, labels, lids or similar coatings. They may be provided with a plastic cap or lid covering the thin metal foil seal which forms one wall of the container. Similarly, the term liquid or liquid contents embraces liquids, or liquids containing solids (e.g., soups, etc.) or even semi-solid or gelatinous materials; i.e., the term liquid in its broadest form encompasses materials which cannot sustain a shear force.

Returning now to FIG. 1, the plastic cup 12 may not be completely full, and an air gap 18 may exist between the liquid 16 and a wall 20 of the plastic cup 12. While the EMAT transducer assembly 10 need not be in contact with the container, for the present invention to work the liquid contents must be in contact with either the thin metal wall or the thin metal foil seal 14 for the vibrations thereof to be able to be fully coupled into the liquid contents 16. If air gaps 18 occur often, it may be necessary to orient (invert) the container 12 to ensure that the force of gravity causes the liquid contents 16 to be in contact with the thin metal wall or metal foil seal 14. In this embodiment, a magnet arrangement 22 for generating magnetic fields in the surface of the metal foil seal 14, parallel to the surface of the metal foil seal 14, is formed by a pair of permanent (advantageously made of neodymium-iron) magnets 24 and 26, and a mild steel yoke 28. The mild steel yoke 28 serves as a low reluctance magnetic field return path. The permanent magnets 24 and 26 are arranged so that the north pole N of one permanent magnet faces the south pole S of the other permanent magnet, with an air gap 30 between them. This arrangement creates strong magnetic fields 32 between faces 34, 36 of the two permanent magnets 24, 26 across the air gap 30. A flexible printed circuit eddy current coil 38 (shown in detail in FIG. 2) is placed above the magnet arrangement 22. The eddy current coil 38 is separated from the permanent magnets 24, 26 by a non-conductive spacer 40 and a thin layer 42 of copper shielding material is placed on top of the permanent magnets 24, 26 between the magnets 24, 26 and the eddy current coil 38 to prevent signal generation in the magnets 24, 26.

Figure 2:
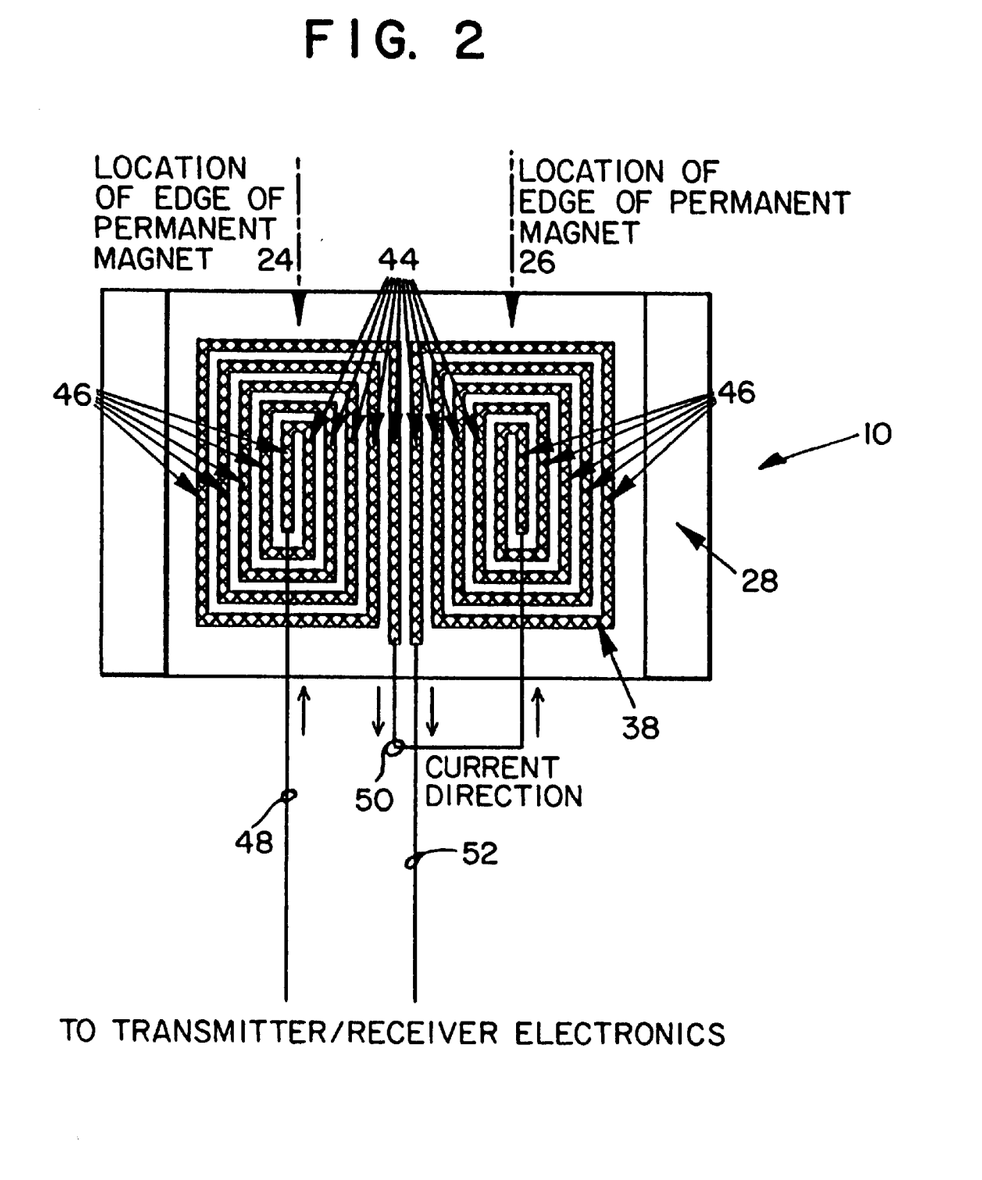
FIG. 2 is a top view of the EMAT transducer assembly of FIG. 1, taken in the directon of arrows 2—2 of FIG. 1, showing a first embodiment of a flexible printed circuit eddy current coil configuration according to the present invention.

FIG. 2 shows how the eddy current coil 38 is connected so that electrical currents flowing in central conductors 44 of the eddy current coil 38 all flow in the same direction, while the electrical currents in outer conductors 46 flow in an opposite direction with respect to those in the central conductors 44. Electrical leads 48, 50 and 52 are provided and connected to the eddy current coil 38 to conduct the electricity to and from the eddy current coil 38. Referring again to FIG. 1, the plastic cup 12 containing the liquid 16 is placed on top of the EMAT transducer assembly 10 as shown. The inspection of the liquid 16 inside the plastic cup 12 with a metal foil lid seal 14 and a non-conductive plastic cap 54 is illustrated. The eddy current coil 38 is electrically connected to a transmitter/receiver unit (not shown) which drives the transducer assembly 10 with a large radio frequency (RF) current tone burst. The RF tone burst induces mirror image eddy currents in the metal foil seal 14 through the non-conductive plastic cap 54. Fringing fields from the magnet arrangement 22 cause large magnetic fields 32 to exist in the metal foil seal 14 essentially parallel to a surface 56 of the metal foil seal 14 and oriented from one magnet face 34 to the other magnet face 36. The two permanent magnets 24, 26 are spaced apart by a distance (i.e., the air gap 30) that creates magnetic fields only in a central region 58 of the metal foil seal 14 that has eddy currents flowing in one direction. The precise distance depends on the strength of the permanent magnets 24, 26 and the geometry, and can be determined experimentally. This is done to create an ultrasonic wave with uniform polarity. Those eddy currents which flow perpendicular to the applied magnetic field 32 create a force normal to the surface 56 of the metal foil seal 14 which launch compressional waves 60 in the liquid 16. These ultrasonic waves 60 travel through the liquid 16 and reflect off a liquid-air interface 62 at an upper portion 64 of the plastic container or cup 12. The ultrasonic waves 60 then travel back down through the liquid 16 and cause the metal foil seal 14 to vibrate. The vibration of the metal foil seal 14 in the presence of the applied magnetic field 32 induces a voltage in the eddy current coil 38. This voltage is detected and conveyed by the electrical leads 48 and 52 to a preamplifier (not shown) and then sent to the is pulser/receiver electronics (also not shown) where it is further amplified and filtered. The detected voltage signal can then be displayed on an oscilloscope (not shown) or captured by a high-speed waveform digitizer (not shown) and processed or displayed by a computer (not shown). By measuring the time of flight of the received signal, and knowing the velocity of sound for the liquid 16 in the plastic container or cup 12, a precise measure of the liquid 16 height H in the plastic container or cup 12 can be made. This method employs the EMAT assembly 10 to launch the ultrasonic compressional waves 60 into the liquid contents 16. The compressional waves 60 travel through the liquid contents 16 and reflect off the liquid-interface 62. The reflected ultrasonic compressional waves 60 return to the thin metal wall 14 and cause it to vibrate in the presence of the magnetic field 32 produced by the EMAT transducer assembly 10. The vibrations of the thin metal wall 14 induce a voltage in the eddy current coil 38. A time of flight of the ultrasonic compressional waves 60 through the liquid contents 16 is measured by noting when the eddy current coil 38 is pulsed, and the time when the ultrasonic compressional waves 60 return and induce the voltage in the eddy current coil 38. Since the liquid contents 16 are known, a calculation of the liquid height H can be calculated using a preestablished value for a velocity of the ultrasonic compressional waves 60 within the liquid contents 16, and measured time of flight as determined by the transmission and reception of the ultrasonic compressional waves 60.

By measuring the signal amplitude, information on the condition of the liquid 16; e.g., whether or not it is spoiled, can be determined. The actual condition measurement involves a comparison of the measured attenuation against preestablished values of attenuation representative of known conditions of the liquid contents. The preestablished values would be obtained through laboratory tests, etc. and would allow comparisons against known standards. The comparisons could be done by a human operator comparing a displayed value of attenuation (a signal strength, etc.) against a table value, or preferably it could be done electronically using a programmed microprocessor-based system employing a look-up table stored in memory. The latter technique would facilitate automation of the method and reduce subjective errors introduced by human operators processing the results.

Figure 3:
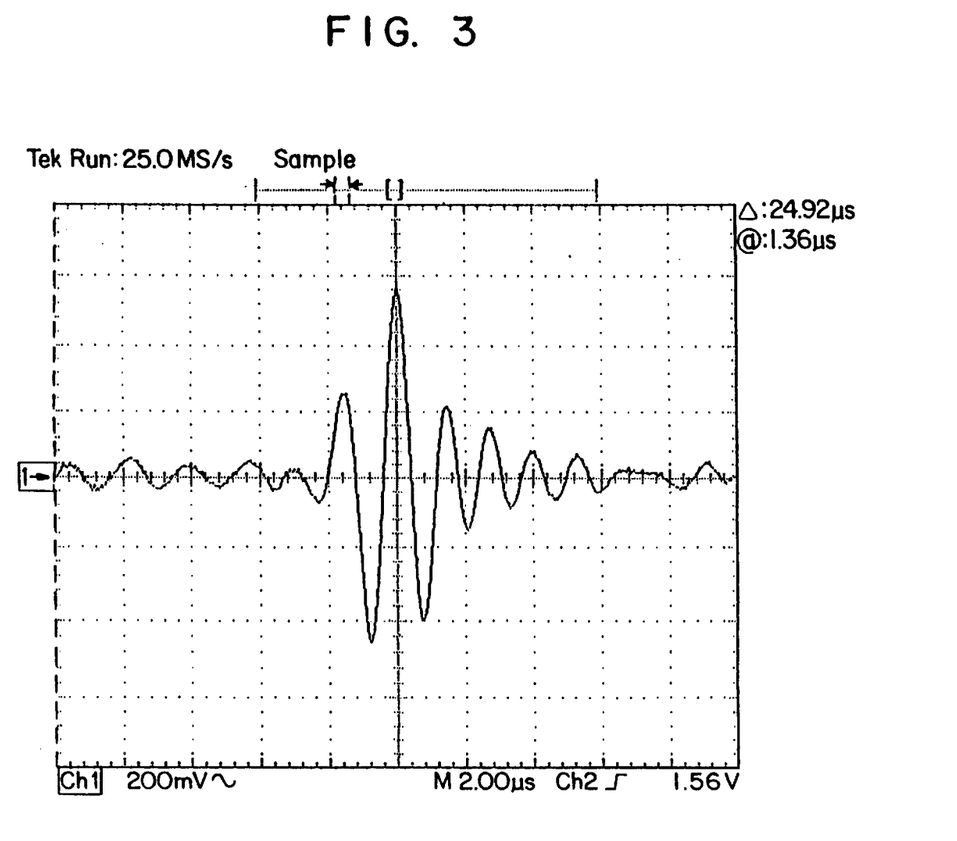
FIG. 3 is a representation of an actual oscilloscope trace showing the signals generated and received in a plastic container with a metal foil seal by the EMAT transducer assembly of FIG. 1.

A prototype EMAT transducer assembly 10 was prepared and used to generate and receive ultrasound in a number of metal or partially metal containers and plastic containers to which a thin layer of copper foil was adhered. FIG. 3 is a representation of an actual oscilloscope trace showing the received signal in a plastic container 12 with a metal foil seal 14, using the embodiment of FIGS. 1 and 2 to both generate and receive the ultrasonic signal. By measuring the time of arrival of the reflected ultrasound pulse, the level of the liquid could be determined. By measuring the signal's amplitude, spoilage of the edible foodstuffs therein due to bacteria growth could be detected because the spoilage caused the detected signal to be attenuated to a greater degree than that which occurred in non-spoiled cases. In fact, cases of severe spoilage actually caused the received signal to disappear. These tests were performed and signals were induced through a cellophane wrapper and a plastic lid approximately 0.030" thick. This type of package precludes the use of conventional ultrasonics to perform the measurements. A prototype EMAT transducer assembly 10 was also used to launch and receive ultrasonic pulses into liquids inside aluminum beverage cans, steel cans, and plastic containers to which a thin metal foil had been adhered. The EMAT transducer assembly 10 was also used to launch and receive signals in liquids contained in rectangular cardboard beverage boxes (i.e., juice boxes) having an interior metal foil lining. Accordingly, the method and apparatus of the present invention has a wide range of potential uses such as automated liquid level sensing, automated liquid condition assessment, high temperature liquid inspections, inspection of hazardous liquids in containers, liquid flow velocity measurements, and the imaging of solids inside liquid containers.

Other embodiments of EMAT transducer assembly configurations for use in the present method are described and shown in FIGS. 4–7. These embodiments involve variations on the shape of the eddy current coil, as well as the structure of the magnet arrangements employed to generate the required magnetic fields. In all of the following embodiments, the EMAT eddy current coil would be located proximate the thin metal wall or metal foil seal 14.

Figure 4A:
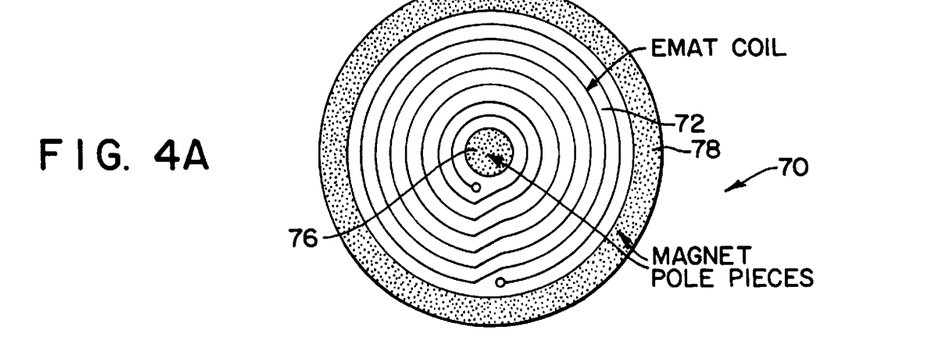
FIGS. 4A and 4B are bottom and side views of a second embodiment of an EMAT transducer assembly according to the present invention.
Figure 4B:
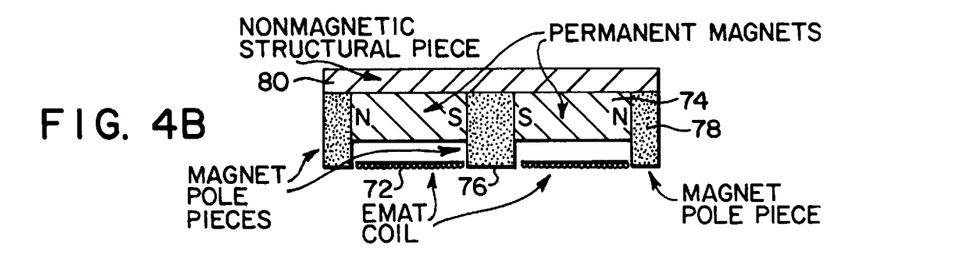

FIGS. 4A and 4B show an embodiment which results in a more efficient EMAT transducer assembly than that of FIGS. 1 and 2. As shown in FIGS. 4A and 4B, EMAT transducer assembly 70 has a circular eddy current coil 72 located proximate to a cup-shaped permanent magnet 74 having an aperture in the center to allow it to be combined with a central cylindrical pole piece 76 and an outer cylindrical pole piece ring 78 to create radially oriented fields. A non-magnetic structural piece 80 may be provided to the connect the several elements together as an assembly, but the magnetic fields of the permanent magnet 74 may be sufficient to hold it together as a unit. In this, as well as the other embodiments, the non-magnetic structural piece may be made of any non-magnetic material; e.g., plastic, ceramic, stainless steel, aluminum, etc. The function of the structural piece is merely as a holder or support; naturally its actual material (so long as it is non-magnetic, even if a conductor) will be selected to withstand the temperature and other environmental factors required by a given application. The embodiment of FIGS. 4A and 4B would be a more efficient EMAT transducer assembly than that described above in connection with FIGS. 1 and 2 because more of the eddy current coil 72 would be active in generating and receiving the ultrasonic sound waves.

Figure 5A:
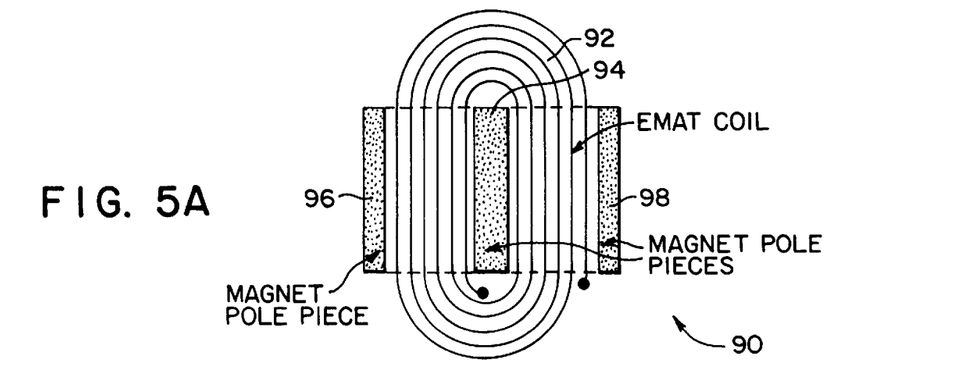
FIGS. 5A and 5B are bottom and side views of a third embodiment of an EMAT transducer assembly according to the present invention.
Figure 5B:
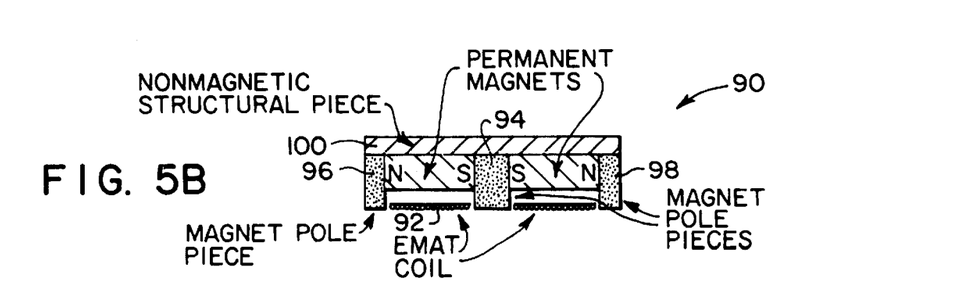

FIGS. 5A and 5B disclose another embodiment of an EMAT transducer assembly 90 which uses a rectangular (racetrack) eddy current coil 92 with a magnet arrangement having a rectangular central pole piece 94 at the middle of the rectangular eddy current coil 92, and rectangular pole pieces 96, 98 at outer edges of the rectangular eddy current coil 92. Again, a non-magnetic structural piece 100 may be provided to provide a rugged, stable transducer assembly. This embodiment causes the magnetic fields in the thin metal wall surface of a container being inspected to be oriented in opposite directions from the center pole piece 94 to the outer pole pieces 96, 98, which results in the induced eddy currents and magnetic fields reversing at the same time, which causes a uniform polarity Lorentz force and created ultrasonic pulse.

Figure 6A:
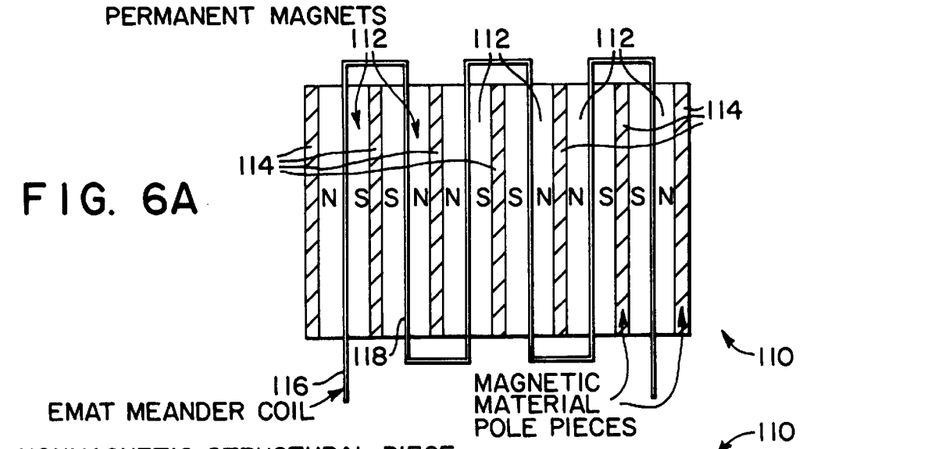
FIGS. 6A and 6B are bottom and side views of a fourth embodiment of an EMAT transducer assembly according to the present invention.
Figure 6B:
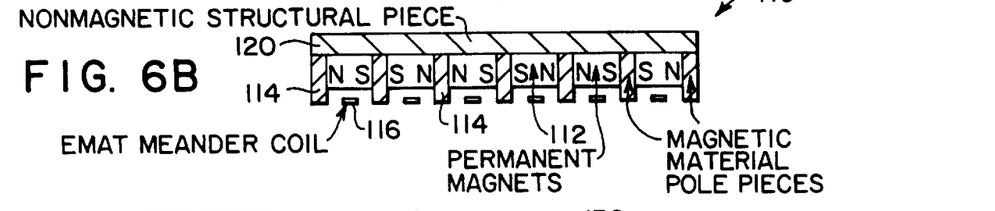

FIGS. 6A and 6B show another embodiment of an EMAT transducer assembly 110 which employs an array of permanent magnets 112 and thin magnetic material pole pieces 114 sandwiched between the permanent magnets 112 such that alternating polarity magnetic fields are created parallel to a surface of the metal or partially metal container. A meander style eddy current coil 116 would then be constructed such that conductors 118 thereof would run between the magnetic pole pieces 114, next to the surface of the container, with the currents and magnetic fields reversing direction together, again resulting in a uniform polarity Lorentz force and resulting ultrasonic pulse. Non-magnetic structural piece 120 may again be provided.

Figure 7A:
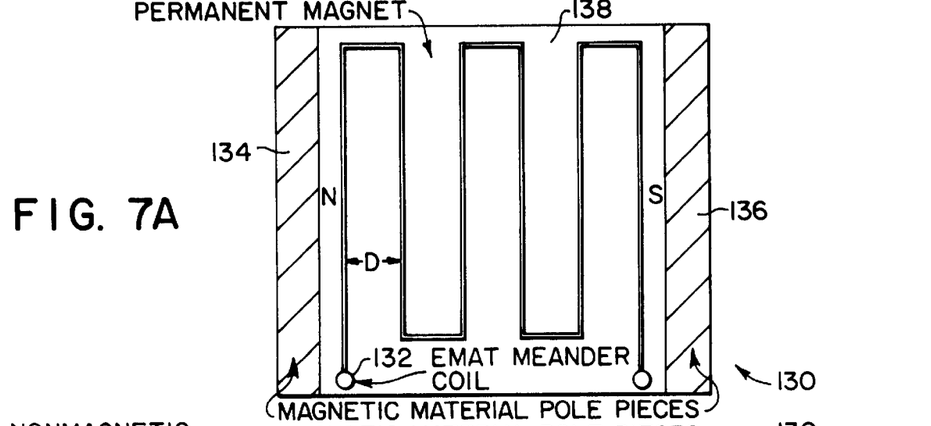
FIGS. 7A and 7B are bottom and side views of a fifth embodiment of an EMAT transducer assembly according to the present invention.
Figure 7B:
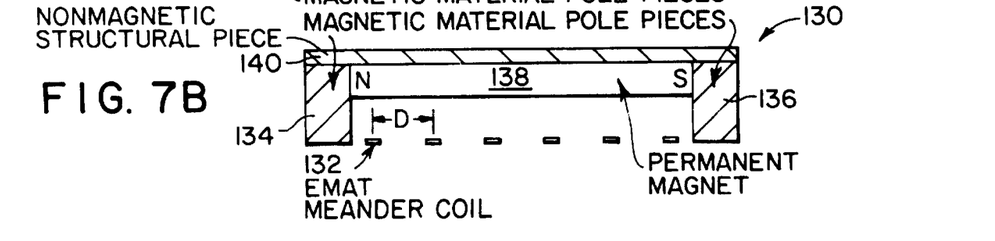

FIGS. 7A and 7B disclose yet still another embodiment of an EMAT transducer assembly, generally referred to as 130, which also employs a meander style eddy current coil 132 located in between two magnetic pole pieces 134, 136 and underneath a single permanent magnet 138. The magnetic field produced would be parallel to the surface of the container being inspected. Non-magnetic structural piece 140 can again be provided. The meander eddy current coil 132 would be driven by an RF toneburst with a frequency given by: $F=V_L/(2D \sin(\theta))$, where F is the frequency of the toneburst, D is the wire to wire (or conductor) spacing in the meander eddy current coil, $V_L$ is the compressional wave velocity in the liquid, and $\theta$ is the ultrasonic beam angle with respect to a line normal to the surface. It would then be possible to sweep the beam (i.e., vary the beam angle) by changing the frequency F of the toneburst. The advantage of this design is that it would allow an operator to locate solids or other sound wave reflectors within the liquid contents 16.

Figure 8:
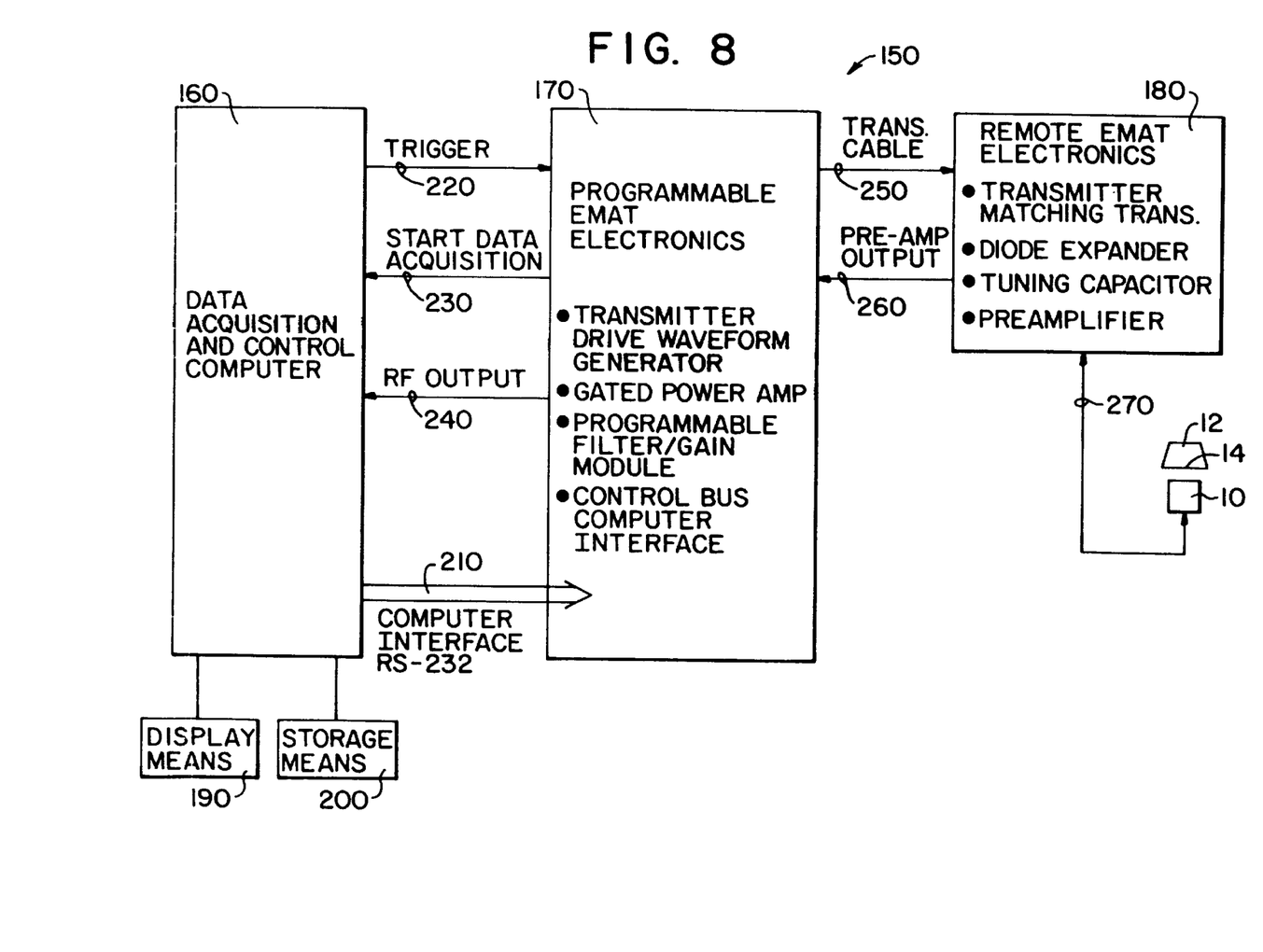
FIG. 8 is a schematic block diagram illustrating an electromagnetic acoustic transducer (EMAT) inspection system for ultrasonically inspecting the liquid contents of a container according to the present invention.

Finally, FIG. 8 schematically discloses an electromagnetic acoustic transducer (EMAT) inspection system 150 for ultrasonically inspecting the liquid contents 16 of a container 12. The system 150 is comprised of four main portions: data acquisition and control computer means 160; programmable EMAT electronics 170; remote EMAT electronics 180; and the EMAT transducer assembly 10. The data acquisition and control computer means 160 is operative to control the settings of various parameters related to the EMAT inspection system, and also serves as the primary operator interface with the system 150. Included therein would be means for digitizing the signals and processing them through known software. Accordingly, data acquisition and control means 160 could comprise a typical personal computer adapted for these purposes. Integral or connected thereto will typically be means for displaying received ultrasonic signals 190 from the container 12, as well as data storage means 200 for retaining the signals as data for later analysis. A computer interface 210 is provided between data acquisition and control computer means 160 and the programmable EMAT electronics 170; a trigger signal is sent via line 220 to the electronics 170, while data acquisition start signals and RF output signals are sent via lines 230 and 240, respectively. Transmitter cable 250 provides the RF toneburst from the programmable EMAT electronics 170 to the remote EMAT electronics 180, while preamplified output signal cable 260 provides the preamplified signals from the EMAT transducer assembly 10 (via the remote EMAT electronics 180) to the programmable EMAT electronics 170. Line 270 interconnects the EMAT transducer assembly 10 with the remote EMAT electronics 180 to provide the RF toneburst signal to the EMAT transducer assembly 10 and to provide the received signals back to the remote EMAT electronics 180.

The method and apparatus of the present invention has several advantages over conventional methods for the inspection of liquids in containers. The method and apparatus can be used to inspect liquids in metal or partially metal containers that have an outer layer of non-conductive material such as paint, wrappers, labels, lids, or coating that would prevent the coupling of ultrasound into the container from a conventional ultrasonic transducer.

A liquid or gel couplant is required for conventional ultrasonic testing of liquids in containers. However, the couplant can be eliminated by using the present disclosure since EMATs are employed, which also facilitates automating inspection of liquids in containers, facilitates the rapid scanning of liquids in containers, and eliminates errors in measurements caused by the use of couplant, as well as eliminating the necessity to clean off the couplant of a container wall after testing. Naturally, the cost of providing the couplant for testing is also eliminated.

The method and apparatus of the disclosure allows liquids in metal or partially metal containers at very high temperatures to be inspected because of the non-contact nature of the transducer. Conventional ultrasonics using liquid or gel couplants are not practical at these temperature extremes.

In some cases, the surface of a container to be inspected may be contaminated with hazardous materials which would cause the couplant used in conventional ultrasonic testing to become contaminated resulting in the necessity to treat it as hazardous material for clean up and disposal. With the use of EMATs, this potential hazard is eliminated.

While specific embodiments of the invention have been shown and described in detail to illustrate the application of the principles of the invention, those skilled in the art will appreciate that changes may be made in the form of the invention covered by the following claims without departing from such principles. For example, the present invention may be applied to new ultrasonic inspection apparatus for the inspection of containers, as well as to the replacement, repair or modification of existing ultrasonic inspection apparatus. As an alternative to the use of permanent magnets, D.C. (Direct Current) operated electromagnets, pulsed electromagnets, or A.C. (Alternating Current) electromagnets could be used. Of course, in some embodiments of the invention, certain features of the invention may sometimes be used to advantage without a corresponding use of the other features and thus all such variations and embodiments properly fall within the scope of the following claims.

I claim:

1. A method of ultrasonically inspecting liquid contents in a container to determine a liquid level H therein, the container having a thin metal wall in contact with the liquid contents and forming at least one wall of the container, comprising the steps of:

providing an electromagnetic acoustic transducer (EMAT) assembly proximate to the thin metal wall to produce and cause a magnetic field to exist therein;

energizing an eddy current coil of the EMAT assembly with an RF toneburst signal of known amplitude and frequency to generate a Lorentz force in the thin metal wall and cause it to vibrate and launch ultrasonic compressional waves into the liquid contents in contact with the thin metal wall;

allowing the compressional waves to travel through the liquid contents and reflect off an interface, the reflected ultrasonic compressional waves returning through the liquid contents to the thin metal wall in contact therewith and causing the thin metal wall to vibrate in the presence of the magnetic field produced by the EMAT transducer assembly, the vibrations of the thin metal wall inducing a voltage in the eddy current coil of the EMAT transducer assembly; and measuring a time of flight of the ultrasonic compressional waves through the liquid contents, and using a preestablished value for a velocity of the ultrasonic compressional waves within the liquid contents, calculating the liquid level H of the liquid contents using the measured time of flight and the preestablished velocity value.

* * * * *